(12) United States Patent
Ramanujam

(10) Patent No.: US 12,112,837 B2
(45) Date of Patent: Oct. 8, 2024

(54) METHOD AND SYSTEM FOR AUTOMATING CLINICAL DATA STANDARDS

(71) Applicant: Ilango Ramanujam, Plainsboro, NJ (US)

(72) Inventor: Ilango Ramanujam, Plainsboro, NJ (US)

( * ) Notice: Subject to any disclaimer, the term of this patent is extended or adjusted under 35 U.S.C. 154(b) by 480 days.

(21) Appl. No.: 17/364,404

(22) Filed: Jun. 30, 2021

(65) Prior Publication Data
US 2023/0005573 A1 Jan. 5, 2023

(51) Int. Cl.
| | |
|---|---|
| G16H 10/40 | (2018.01) |
| G06F 40/20 | (2020.01) |
| G06N 20/00 | (2019.01) |
| G16H 10/20 | (2018.01) |
| G16H 40/20 | (2018.01) |

(52) U.S. Cl.
CPC ............ *G16H 10/20* (2018.01); *G06F 40/20* (2020.01); *G06N 20/00* (2019.01); *G16H 40/20* (2018.01)

(58) Field of Classification Search
CPC ........ G16H 10/20; G16H 40/20; G16H 15/00; G16H 10/60; G06F 40/20; G06F 40/169; G06F 40/174; G06N 20/00; G06N 5/022
See application file for complete search history.

(56) References Cited

U.S. PATENT DOCUMENTS

| | | | |
|---|---|---|---|
| 9,842,139 B1 * | 12/2017 | Cohen | G16Z 99/00 |
| 2010/0299335 A1 | 11/2010 | Gopalakrishnan et al. | |
| 2013/0110553 A1 | 5/2013 | Navani et al. | |
| 2018/0060538 A1 * | 3/2018 | Tiwari | G16H 10/60 |
| 2018/0101584 A1 * | 4/2018 | Pattnaik | G06F 9/38 |
| 2018/0349565 A1 * | 12/2018 | Yang | G16H 15/00 |
| 2019/0156921 A1 | 5/2019 | Kohli et al. | |

(Continued)

FOREIGN PATENT DOCUMENTS

| | | | | |
|---|---|---|---|---|
| WO | WO-2016033493 A1 * | 3/2016 | | G06F 17/30294 |

OTHER PUBLICATIONS

Brand, A Model Data Management Plan Standard Operating Procedure: Results From the DIA Clinical Data Management Community, Committee on Clinical, 2015, Therapeutic Innovation & Regulatory Science, pp. 720-729. (Year: 2015).*

*Primary Examiner* — Christopher L Gilligan
(74) *Attorney, Agent, or Firm* — Ashok Tankha

(57) ABSTRACT

A method and a clinical data standards (CDS) automated system are provided for automating clinical data standards and generating study data tabulation model (SDTM) artifacts required for a regulatory submission process using a machine learning model and a natural language processing (NLP) engine with minimal user intervention. The CDS automated system extracts metadata from multiple raw datasets automatically using NLP and feeds the extracted metadata into the machine learning model; predicts automatic case report form (CRF) annotations on the extracted metadata and records new learnings onto the CDS automated system; maps one or more raw datasets against a target SDTM variable; generates an SDTM statistical analysis system (SAS) code, an SDTM specification, and one or more SDTM datasets; generates a define package; validates the generated define package and the SDTM artifacts generated throughout the entire cycle; and generates validation reports in real time.

7 Claims, 8 Drawing Sheets

(56) References Cited

U.S. PATENT DOCUMENTS

| | | |
|---|---|---|
| 2020/0105379 A1 | 4/2020 | Pandita et al. |
| 2021/0090693 A1* | 3/2021 | Burns et al. |
| 2022/0076078 A1* | 3/2022 | Vdovjak ................ G06N 3/08 |
| 2022/0129485 A1* | 4/2022 | Mian .................... G06F 18/217 |
| 2022/0172805 A1* | 6/2022 | Liu ....................... G06N 20/00 |

* cited by examiner

METHOD AND SYSTEM FOR AUTOMATING CLINICAL DATA STANDARDS

BACKGROUND

Global regulatory agencies have clearly embraced data standards from the submission of data, laying the groundwork for expanded adoption, to data collection, tabulation, and analysis. Collecting data in a standardized way is a step for reducing disorganized, time-wasting efforts that may negatively impact patient safety, development timelines, and resource utilization. Manual data entry based on paper-and-pen case report forms (CRFs) followed by a chart review is the conventional way of clinical trial data collection. However, with the development of health care information technology, electronic data capture (EDC) systems accelerate the clinical data collection process and assure data quality with real-time data entry, review, analysis, and verification. Driven by the prevalent use of EDC systems, CRFs gradually transitioned from paper to electronic forms. Many studies have suggested that data entry using electronic CRF (eCRF) applications of EDC systems may achieve higher efficiency and accuracy at a lower cost than the conventional paper-and-pen approach. However, neither EDC nor eCRF fundamentally changed the methods of collecting data. Researchers still need to manually transcribe the data one by one from electronic medical records (EMRs), especially for observational trials using patient data. The data entry process takes time and becomes a significant efficiency bottleneck.

The growing interest in observational trials using patient data from electronic medical records (EMRs) poses challenges to both efficiency and quality of clinical data collection and management. Even with the help of electronic data capture systems and electronic case report forms (eCRFs), the manual data entry process followed by a chart review is still time consuming. Guidance published by the US Food and Drug Administration (FDA) in July 2018, titled "Use of Electronic Health Record Data in Clinical Investigations Guidance for Industry", promoted the idea of secondary use of source data at the time of care to prepopulate eCRFs without specific user efforts. The guidance focused more on the use of structured data, for example, demographics, vital signs, and laboratory data, but little on the use of unstructured clinical narratives, which account for about 80% of patient care information. To achieve data interoperability for these unstructured clinical narratives, many electronic data capture (EDC) systems created predesigned patient information templates including standardized documentation or forms for coded data entry in lieu of free text documentation to structuralize the medical records. Clinicians record patient information under the guidance of these patient information templates, and at the same time, the EDC systems store the coded data from the patient information templates for future analysis. Patient information templates assist in data collection for research and patient care, integrate EDC systems and EMRs, and automatically prepopulate the eCRF. However, there are obvious limitations to the patient information templates. For clinicians, the one-size-fits-all templates restrict freedom of expression. For researchers, predesigned data elements limit usability of the data in different research topics. The development of natural language processing (NLP) technologies provides new potential for better secondary use of free unstructured EMR data.

Pharmaceuticals are strictly regulated by government agencies, for example, the U.S. Food and Drug Administration (FDA). The regulation process involves extensive clinical research and testing to demonstrate the safety and efficacy of new drugs and devices before they can be approved for commercial use. In the pharmaceutical industry, health care data is available in multiple physical formats. The reason for the presence of health care data in multiple physical formats could be attributed to rules such as the regulatory requirements for capturing data in electronic data capture (EDC) systems, study design, different technology vendors, etc. It is challenging to combine and build comprehensive business intelligence from data originating from these disparate systems and formats. Clinical data standards automation improves the accuracy of results in the clinical trial process and discards manual processes, for example, creating forms and annotations by hand or entering data manually onto a spreadsheet. Clinical data standards automation also makes it easier to comply with the standards required by regulatory authorities.

Hence, there is a long-felt need for a method and a system for automating clinical data standards and generating study data tabulation model (SDTM) artifacts required for a regulatory submission process using a machine learning model and a natural language processing engine with minimal user intervention.

SUMMARY

This summary is provided to introduce a selection of concepts in a simplified form that are further disclosed in the detailed description. This summary is not intended to determine the scope of the claimed subject matter.

The method and the system disclosed herein address the above recited need for automating clinical data standards and generating study data tabulation model (SDTM) artifacts required for a regulatory submission process using a machine learning model and a natural language processing engine with minimal user intervention. The method employs a clinical data standards (CDS) automated system comprising at least one processor configured to execute computer program instructions for automating clinical data standards and generating SDTM artifacts required for the regulatory submission process using a machine learning model and a natural language processing engine with minimal user intervention. The CDS automated system extracts metadata from multiple raw datasets automatically using natural language processing and feeds the extracted metadata into the machine learning model. The natural language processing engine preprocesses text information before feeding the processed text information into the machine learning model. The CDS automated system predicts one or more automatic case report form (CRF) annotations on the extracted metadata using the machine learning model and records new leanings on to the CDS automated system with minimal user intervention. The machine learning model predicts appropriate CRF annotations based on annotated metadata information available in the CDS automated system and information acquired from previous learnings. The previous leanings are leanings recorded by the CDS automated system based on the annotated metadata information acquired from a user for the first time.

The clinical data standards (CDS) automated system maps one or more raw datasets against a target study data tabulation model (SDTM) variable based on the extracted metadata available in the CDS automated system and the information acquired from the previous learnings. The CDS automated system generates a study data tabulation model (SDTM) statistical analysis system (SAS) code, an SDTM specification, and one or more SDTM datasets based on the mappings. The CDS automated system generates a define package based on the annotated metadata information and the mappings available in the CDS automated system. The machine learning model identifies appropriate derivations and generates the SDTM SAS code based on the derivations. The CDS automated system validates the generated define package and one or more SDTM artifacts generated throughout an entire cycle and generates validation reports in real time. The SDTM artifacts comprise, for example, Define.xml files, stylesheets, SDTM datasets, an annotated case report form (CRF), a reviewers guide, and other supporting documents.

In one or more embodiments, related systems comprise circuitry and/or programming for executing the methods disclosed herein. The circuitry and/or programming are any combination of hardware, software, and/or firmware configured to execute the methods disclosed herein depending upon the design choices of a system designer. In an embodiment, various structural elements are employed depending on the design choices of the system designer.

BRIEF DESCRIPTION OF THE DRAWINGS

The foregoing summary, as well as the following detailed description, is better understood when read in conjunction with the appended drawings. For illustrating the invention, exemplary constructions of the invention are shown in the drawings. However, the invention is not limited to the specific methods and components disclosed herein. The description of a method step or a component referenced by a numeral in a drawing is applicable to the description of that method step or component shown by that same numeral in any subsequent drawing herein.

FIG. 4 exemplarily illustrates a screenshot of a graphical user interface provided by the clinical data standards automated system, displaying an electronic case report form (eCRF) with possible annotations.

FIG. 5 exemplarily illustrates a screenshot of a graphical user interface provided by the clinical data standards automated system, displaying a smart mapper that maps one or more raw datasets against a target SDTM variable.

FIG. 6 exemplarily illustrates a screenshot of the smart mapper displaying a mapping of one or more raw datasets against the target SDTM variable with mapping comments.

DETAILED DESCRIPTION

Figure 1:
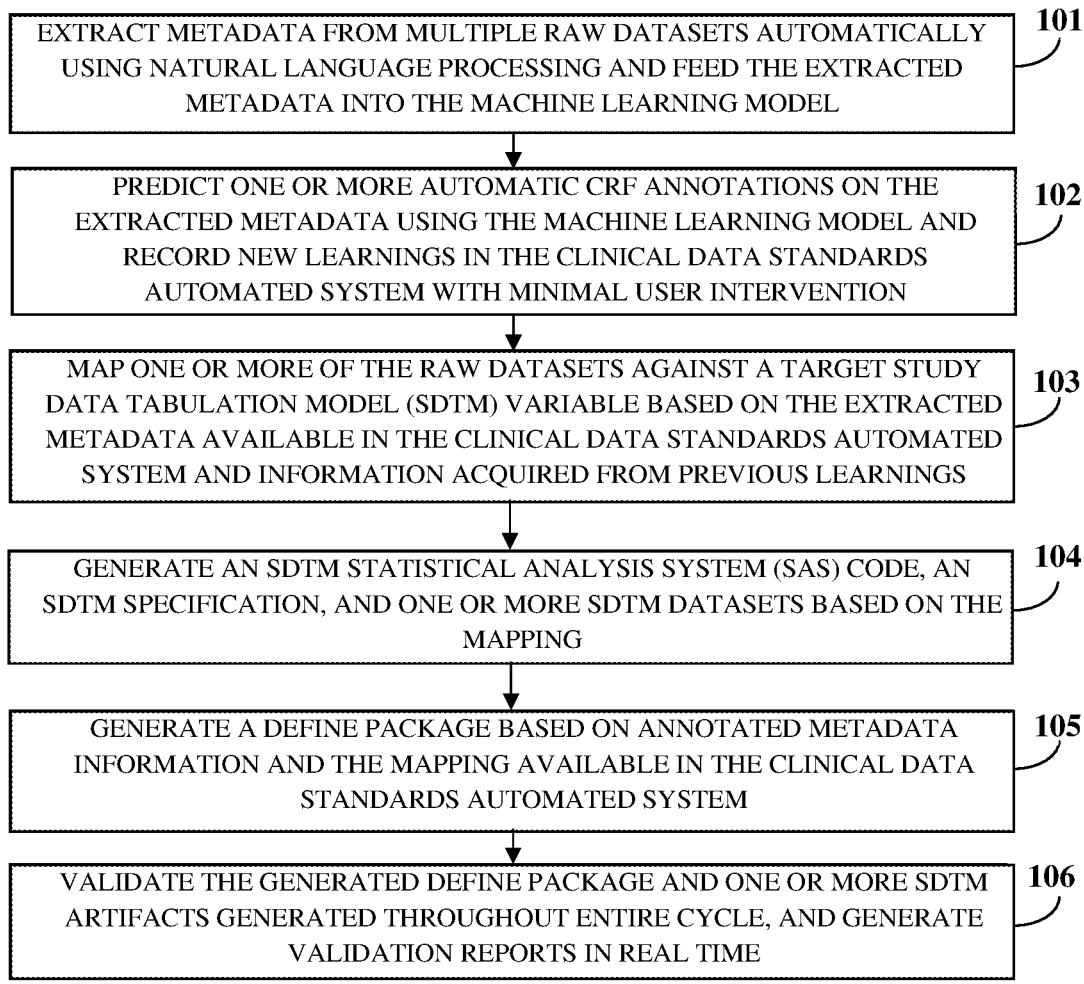
FIG. 1 illustrates a method for automating clinical data standards and generating study data tabulation model (SDTM) artifacts required for a regulatory submission process using a machine learning model and a natural language processing engine with minimal user intervention.

FIG. 1 illustrates a method for automating clinical data standards and generating study data tabulation model (SDTM) artifacts required for a regulatory submission process using a machine learning model and a natural language processing engine with minimal user intervention. As used herein, "SDTM" refers to a standard structure for human clinical trial or study data tabulations and for non-clinical study data tabulations that are to be submitted as part of a product application to a regulatory authority such as the United States Food and Drug Administration (FDA). The data used in the SDTM is consistent and minimizes the chance of errors. The data consistency in the SDTM ensures cross-study and cross-organization pooling and improved analysis, which helps reviewers quickly understand the data, leading to fewer questions and a faster approval in order to submit SDTM artifacts to a regulatory board. SDTM defines the standardized domains for submitting clinical data, thereby providing the regulatory authority with a consistent method of viewing the clinical data. The core SDTM model comprises different classes of domains, for example, events, interventions, and findings. Each domain comprises a number of possible variables. The actual domains and variables required to represent the non-clinical data is different compared to the clinical data. The Clinical Data Interchange Standards Consortium (CDISC) recommends the Standard for Exchange of Non-clinical Data (SEND) for the non-clinical data. The SEND defines standard domains and variables to be used when submitting non-clinical data to the regulatory board.

The method disclosed herein employs a clinical data standards (CDS) automated system comprising at least one processor configured to execute computer program instructions for automating clinical data standards and generating study data tabulation model (SDTM) artifacts required for a regulatory submission process, using a machine learning model and a natural language processing engine with minimal user intervention. The CDS automated system is a metadata-driven artificial intelligence system configured to automate the clinical data standards and submission process. The CDS automated system generates reliable and precise results that provide a substantial benefit to pharmaceutical industries, biotech industries, the Contract Research Organization (CRO), etc. The CDS automated system is a metadata multi-level management system. The multi-level management system comprises a global level and a project level. The CDS automated system generates SDTM artifacts required for a regulatory submission process with minimal user input, for example, study data and a blank Case Report Form (CRF). As used herein, "CRF" refers to a paper or electronic questionnaire specifically used in clinical trial research. CRFs contain data obtained during a patient's participation in a clinical trial. A sponsor of the clinical trial develops the CRF to collect specific data they need in order to test their hypotheses or answer their research questions. The size of the CRF ranges from a handwritten one-time snapshot of a patient's physical condition to hundreds of pages of electronically captured data obtained over a period of weeks or months. The metadata driven machine learning and natural language processing engine assists the CDS automated system to learn study-based information with minimal user intervention, improves annotation results, and maps continuously on every subsequent study.

In the method disclosed herein, the clinical data standards (CDS) automated system extracts 101 metadata from multiple raw datasets automatically using natural language processing and feeds the extracted metadata into the machine learning model. As used herein, metadata is data which describes information about any raw data that is being entered into the CDS automated system using natural language processing methods. In an embodiment, the CDS automated system converts raw metadata into standardized, Standard for Exchange of Non-clinical Data (SEND) data similar to conversion of raw data into study data tabulation model (SDTM) datasets. The natural language processing (NLP) engine preprocesses text information before feeding the processed text information into the machine learning model. The NLP engine extracts the required intend, for example, sentences, from a questionnaire available in several case report forms (CRFs), for example, pages, as part of preprocessing of the text information performed in the CDS automated system. The questionnaire comprises sentences received from a user. The NLP engine uses the extracted text for the preprocessing steps performed in the CDS automated system. In this example, the input to the NLP engine is the preprocessed text and the output is the intends from the NLP engine. The CDS automated system predicts the intend of the questionnaires in the CRF.

The clinical data standards (CDS) automated system predicts 102 one or more automatic case report form (CRF) annotations on the extracted metadata using the machine learning model and records new leanings in the CDS automated system with minimal user intervention. The machine learning model predicts appropriate CRF annotations based on annotated metadata information available in the CDS automated system and information acquired from previous learnings. The previous leanings are learnings recorded by the CDS automated system based on the annotated metadata information acquired from a user for the first time. In an embodiment, any questionnaire that is unknown to the CDS automated system is annotated by a user for the first time. The CDS automated system records the leanings from the questionnaire in the background and applies the learnings in subsequent studies. The CDS automated system significantly reduces manual intervention based on the continuous learning and reuse capabilities of the CDS automated system. The extracted metadata is pre-filled in a blank CRF. The CDS automated system extracts and preprocesses the contents of the CRF automatically using natural language processing methods prior to importing the contents into the machine learning model. The CDS automated system utilizes the preprocessed metadata in the machine learning (ML) model to predict appropriate CRF annotations. The machine learning model predicts appropriate CRF annotations based on the annotated metadata information available in the CDS automated system and the information acquired from the previous learnings.

In an embodiment, the clinical data standards (CDS) automated system extracts metadata, for example, text information, and attributes from a blank case report form (CRF). The blank CRF is, for example, in a Portable Document Format (PDF). The CDS automated system stores the extracted metadata in a structured machine-readable format. The CDS automated system performs preprocessing steps on the extracted text and the attributes. After preprocessing performed by the CDS automated system, the machine learning (ML) model predicts appropriate CRF annotations for the extracted text and the attributes. The ML model sends the predicted CRF annotations and their corresponding text and the attributes to an application in the CDS automated system. The application in the CDS automated system inserts the appropriate CRF annotations based on the ML prediction at the right location in the blank CRF. The CDS automated system allows a user to annotate the extracted text and the attributes manually in case of any inappropriate or missing annotation performed by the CDS automated system. The ML model learns from the manual interventions on the annotation.

In an embodiment, the clinical data standards (CDS) automated system sorts, organizes, and uses the collected information, that is, the metadata extracted from the raw datasets as a raw dataset that in turn improves the raw to target mapping process. The CDS automated system maps 103 one or more of the raw datasets against a target study data tabulation model (SDTM) variable based on the extracted metadata available in the CDS automated system and the information acquired from the previous leanings. The metadata extracted from the raw datasets comprises the information collected from the user. The CDS automated system uses the raw dataset to map the appropriate target SDTM variable. The CDS automated system improves the mapping accuracy by utilizing the annotation information received from the annotated case report form (CRF) or an electronic CRF (eCRF) configured by the CDS automated system. In an embodiment, the CDS automated system automatically matches the raw dataset against the target SDTM variables based on the annotated metadata information available in the CDS automated system as well as from a knowledge base.

The clinical data standards (CDS) automated system generates 104 a study data tabulation model (SDTM) statistical analysis system (SAS) code based on the mapping. The CDS automated system also generates 105 a define package based on the annotated metadata information and the mappings available in the CDS automated system. In an embodiment, the CDS automated system extracts the metadata automatically based on the SDTM SAS code specification. The CDS automated system generates an SDTM SAS code based on the mapping predictions and derivations. The machine learning model is used to identify an appropriate derivation from a derivation repository. In an embodiment, the CDS automated system extracts the metadata from the raw dataset. In another embodiment, the raw metadata is directly imported into the CDS automated system. The CDS automated system performs preprocessing steps on the extracted metadata. The machine learning model identifies and maps the corresponding target variables based on the raw metadata information acquired by the CDS automated system from the previous step. In an embodiment, the CDS automated system allows a user to perform manual mapping for the unmapped raw metadata information and inappropriate mapping combinations generated by the CDS automated system. The CDS automated system learns from the manual intervention and applies the new learnings in subsequent studies. The CDS automated system predicts appropriate derivation logic wherever applicable based on the mapping combinations, study design, and the extracted metadata from the derivation repository. In the method disclosed herein, the CDS automated system generates the following outcomes: SAS programs that are executable by programmers to generate SDTM datasets outside the CDS automated system in an SAS application for submission, and the CDS automated system-generated SDTM datasets that do not require the SAS application.

The clinical data standards (CDS) automated system generates a standalone study data tabulation model (SDTM) statistical analysis system (SAS) code automatically based on the mappings performed in the previous steps. A sample code generated by the CDS automated system is provided below.

```
Study              Study 002
Program Name       DM.sas
Purpose            To create SDTM Dataset DM
Author             XYZ System Generated
Date Created       2020 Nov. 30
Options validvarname = upcase source2 mprint missing = ' ' ;
proc sql;
   create table progpath as
   select fileref, xpath
   from dictionary .extfiles
   where fileref like '#LN%'
   order by fileref;
quit;
data_null;
   set progpath nobs =howmany point = howmany;
   temp = left(reverse (lowcase(xpath)));
   prog =substr (temp, 5, index (temp, '\') -5);
   path =substr (temp, index(temp, '\'));
   prog = left (reverse (prog));
   path = left (reverse (path));
   call symput ('progname', trim(prog));
   call symput ('progpath', trim(path));
   stop;
run;
%put &progname;
%put &progpath;
%include "&progpath. . .\macros\setup.sas";
/*source datasets*/
Data MNL DEMOGRAPHICS;
   length
      STUDYID $200
      USUBJID $200
      SUBJID $200
      SITEID $200
```

The clinical data standards (CDS) automated system validates 106 the generated define package and one or more SDTM artifacts generated throughout an entire cycle and generates validation reports, for example, warning and exception reports, in real time. The cycle, as used herein, refers to a development and review cycle. In an embodiment, the CDS automated system comprises a define package generator that uses information received from components such as an electronic CRF (eCRF) and a smart mapper of the CDS automated system exemplarily illustrated in FIG. 2, to generate a Clinical Data Interchange Standards Consortium (CDISC) standard define.xml and a reviewer's guide, where "define.xml" is an extensible markup language (XML) document that describes the structure and contents, for example, metadata definitions, of the data collected during a clinical trial process. The define package generator generates a define package that is downloadable whenever required. The SDTM artifacts generated by the CDS automated system comprise the define.xml file, stylesheets, SDTM datasets, annotated CRFs, reviewers guide, and other supporting documents. The CDS automated system performs validations based on the CDISC or the US Food and Drug Administration (FDA)-published validation rules. These validations proactively identify conformance issues before the generation of final artifacts, thereby saving time of a user who is involved in the SDTM dataset generation process.

Figure 2:
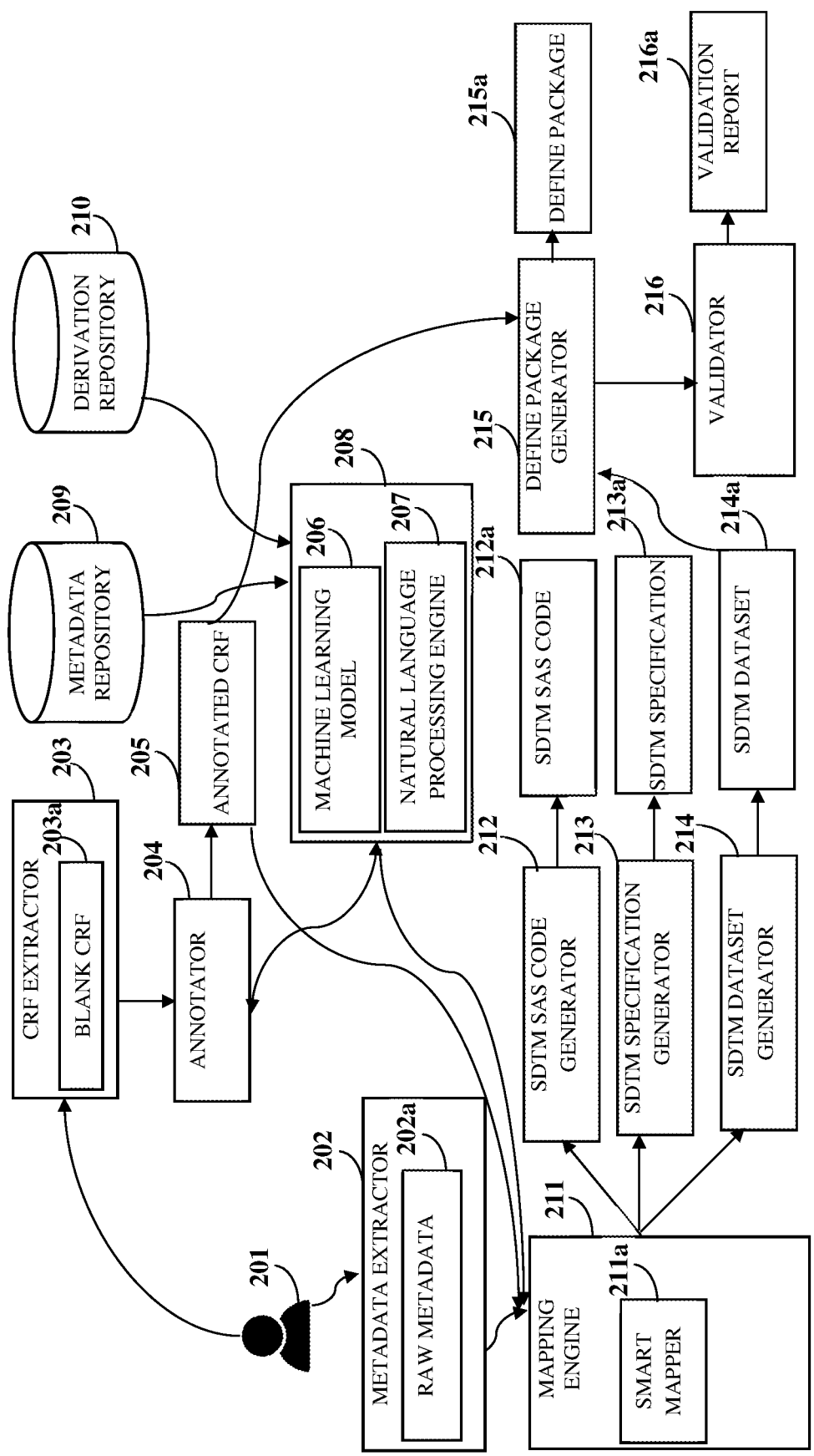
FIG. 2 exemplarily illustrates a flow diagram comprising different components of a clinical data standards automated system.

FIG. 2 exemplarily illustrates a flow diagram comprising different components of the clinical data standards (CDS) automated system. In an embodiment, the components of the CDS automated system comprise a metadata extractor 202, a case report form (CRF) extractor 203, an annotator 204, a mapping engine 211, a machine learning (ML)/natural language processing (NLP) engine 208, a metadata repository 209, a derivation repository 210, a study data tabulation model (SDTM) statistical analysis system (SAS) code generator 212, an SDTM specification generator 213, an SDTM dataset generator 214, a define package generator 215, and a validator 216. An ML model 206 and an NLP engine 207 constitute the ML/NLP engine 208. In an embodiment, the CDS automated system receives raw metadata 202a from a user 201 using NLP methods. The raw metadata 202a is, for example, any raw data comprising user information or any clinical data record of the user 201. In another embodiment, the CDS automated system extracts the metadata and attributes from the user 201 using the metadata extractor 202. The CDS automated system pre-fills the extracted metadata in a blank CRF 203a using the CRF extractor 203.

The annotator 204 automatically annotates the contents in the blank case report form (CRF) 203a. The clinical data standards (CDS) automated system allows the user 201 to annotate the contents in the blank CRF 203a for the first time if there is any unknown data present in the blank CRF 203a. The CDS automated system then records these annotations for future learnings with minimal user interventions. A CRF annotation engine in the annotator 204 assists the CDS automated system to identify relevant trained information and performs all possible appropriate CRF annotations in the blank CRF 203a by using the natural language processing (NLP) engine 207. If the user 201 performs any manual annotations on the blank CRF 203a, the CDS automated system adds those annotations to a knowledge base for reusability. The CDS automated system performs preprocessing steps on the annotated CRF 205 using NLP methods before loading the annotated CRF 205 on to the machine learning model 206. The machine learning model 206 predicts appropriate CRF annotations based on the metadata available in the metadata repository 209 of the CDS automated system. The CDS automated system maps a raw dataset against a target study data tabulation model (SDTM) variable based on the annotated CRF 205 as well as from the previous leanings using the mapping engine 211. A smart mapper 211a in the mapping engine 211 automatically fetches domains and variable annotations in the electronic CRF.

The clinical data standards (CDS) automated system generates a statistical analysis system (SAS) code based on the mapped metadata predictions and derivations using the study data tabulation model (SDTM) SAS code generator 212. The machine learning model 206 identifies appropriate derivations from the derivation repository 210. The CDS automated system also generates an SDTM specification 213a and SDTM datasets 214a based on the mapped raw metadata using the SDTM specification generator 213 and the SDTM dataset generator 214 respectively. The machine learning/natural language processing engine 208 maps the SDTM/Sponsor defined-target to the raw metadata based on the trained historical data. The CDS automated system generates the SDTM dataset 214a along with the mapping specification and standalone SAS program for each domain.

The clinical data standards (CDS) automated system generates a define package 215a based on the annotated CRF 205 and mapped metadata using the define package generator 215. The define package 215a comprises define.xml files. The CDS automated system validates the generated define package 215a and the SDTM artifacts throughout the entire cycle using the validator 216. The validator 216 generates validation reports 216a in real time. The CDS automated system exports the define package 215a from the define package generator 215. The define package 215a further comprises the mapping specification 213a, the SDTM dataset 214a, the annotated CRF 205, and the define.xml file for submission. The CDS automated system validates all the validation guidelines from the Food and Drug Administration (FDA), Pharmaceuticals and Medical Devices Agency (PMDA), and any other regulatory authorities progressively across all the modules throughout the SDTM conversion process.

The annotator 204 automatically annotates the blank case report form (CRF) 203a based on the Clinical Data Interchange Standards Consortium (CDISC) or the sponsor metadata available in the clinical data standards (CDS) automated system. The annotation model in the CDS automated system helps to maintain and improve the annotation attributes that can be reused efficiently with the help of the machine learning model 206 and the natural language processing engine 207. The smart mapper 211a in the mapping engine 211 provides, for example, about seventy five percent of study data tabulation model (SDTM) conversion and saves the mapping time. The CDS automated system is pre-loaded with the CDISC metadata and the control terminologies. The CDS automated system works with any electronic data capture (EDC) raw data. The CDS automated system generates a specification and standalone SAS program per dataset.

The define package 215a in the clinical data standards automated system significantly eliminates manual tasks, easily maps and re-uses sponsor defined metadata standards with the clinical data interchange standards consortium (CDISC) metadata, promotes and re-uses all study metadata, and reduces the need for high expertise technology and processes. The validator 216 performs a data review and executes conformance before the generation of the submission file. In an embodiment, the validator 216 validates added rules to confirm data quality and review. The validator 216 allows rule selection and execution based on a sponsor's requirement. The validator 216 performs issue management and exception handling while generating the define.xml file for completed and on-going studies.

Figure 3:
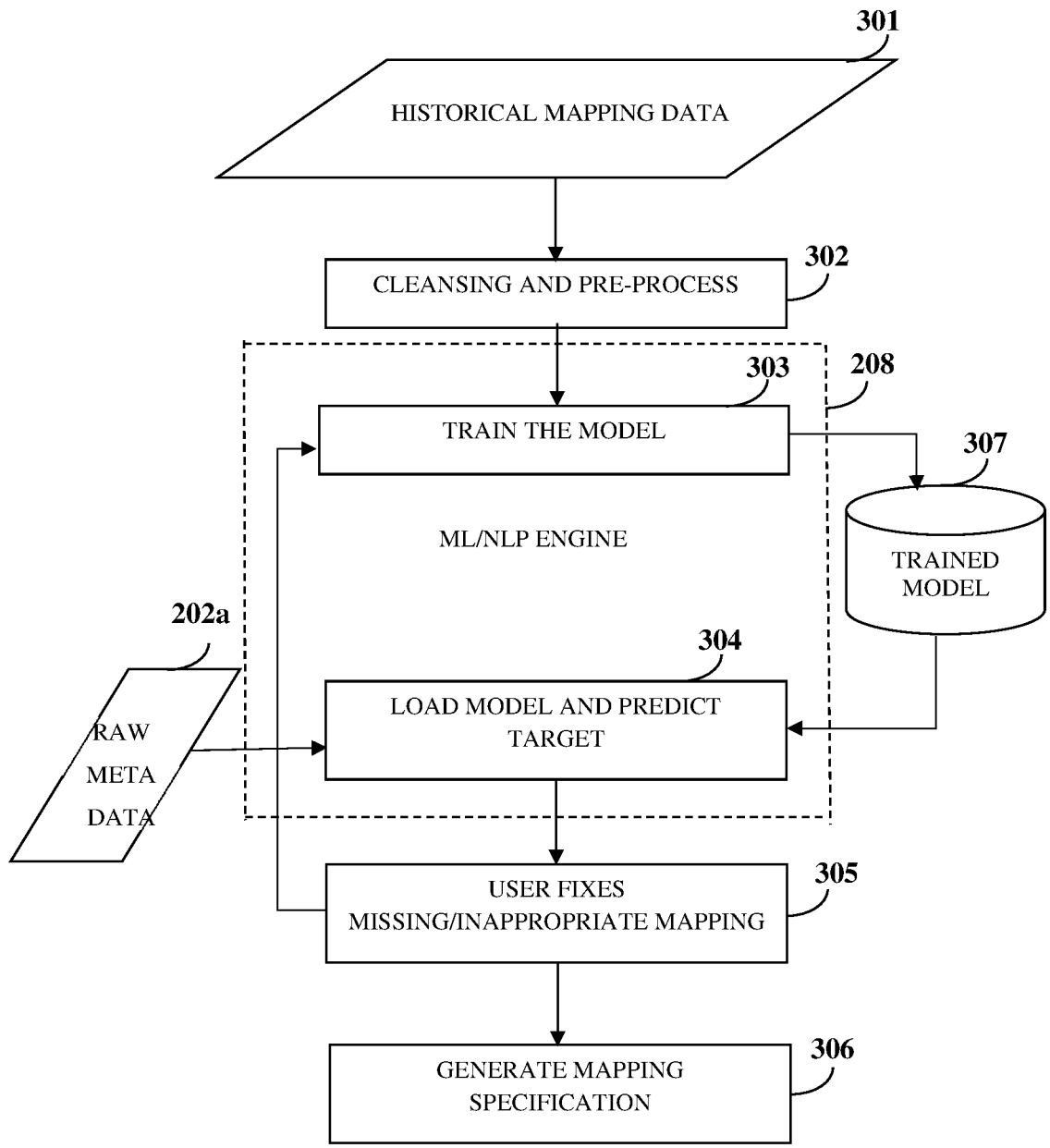
FIG. 3 exemplarily illustrates a flow diagram comprising the steps performed by a machine learning and natural language processing engine of the clinical data standards automated system.

FIG. 3 exemplarily illustrates a flow diagram comprising the steps performed by the machine learning (ML)/natural language processing (NLP) engine 208 of the clinical data standards (CDS) automated system. The CDS automated system performs preprocessing 302 steps before loading raw metadata 202a on to the ML/NLP engine 208. The ML/NLP engine 208 maps the raw metadata 202a to the target study data tabulation model (SDTM) or sponsor defined model based on the historical mapping 301 of the metadata available in the CDS automated system. The ML/NLP engine 208 loads the mapped metadata on to the ML model after the preprocessing steps, thereby training 303 the ML model and generating a trained model 307. The ML/NLP engine 208 receives raw metadata 202a, loads 304 the trained model 307, and predicts the study data tabulation model (SDTM) target for the raw metadata 202a based on the historical mapping 301 of the metadata available in the clinical data standards (CDS) automated system. The trained model 307 predicts 304 appropriate case report form (CRF) annotations based on the metadata available in the CDS automated system and the information acquired from users from previous studies. The CDS automated system allows a user to fix any missing or inappropriate mapping 305 against the target SDTM variable. The CDS automated system then records the fixed mappings as new learnings for subsequent studies, thereby minimizing user intervention. The CDS automated system generates 306 the SDTM specification based on the mapped metadata to generate validation reports in real time.

Figure 4:
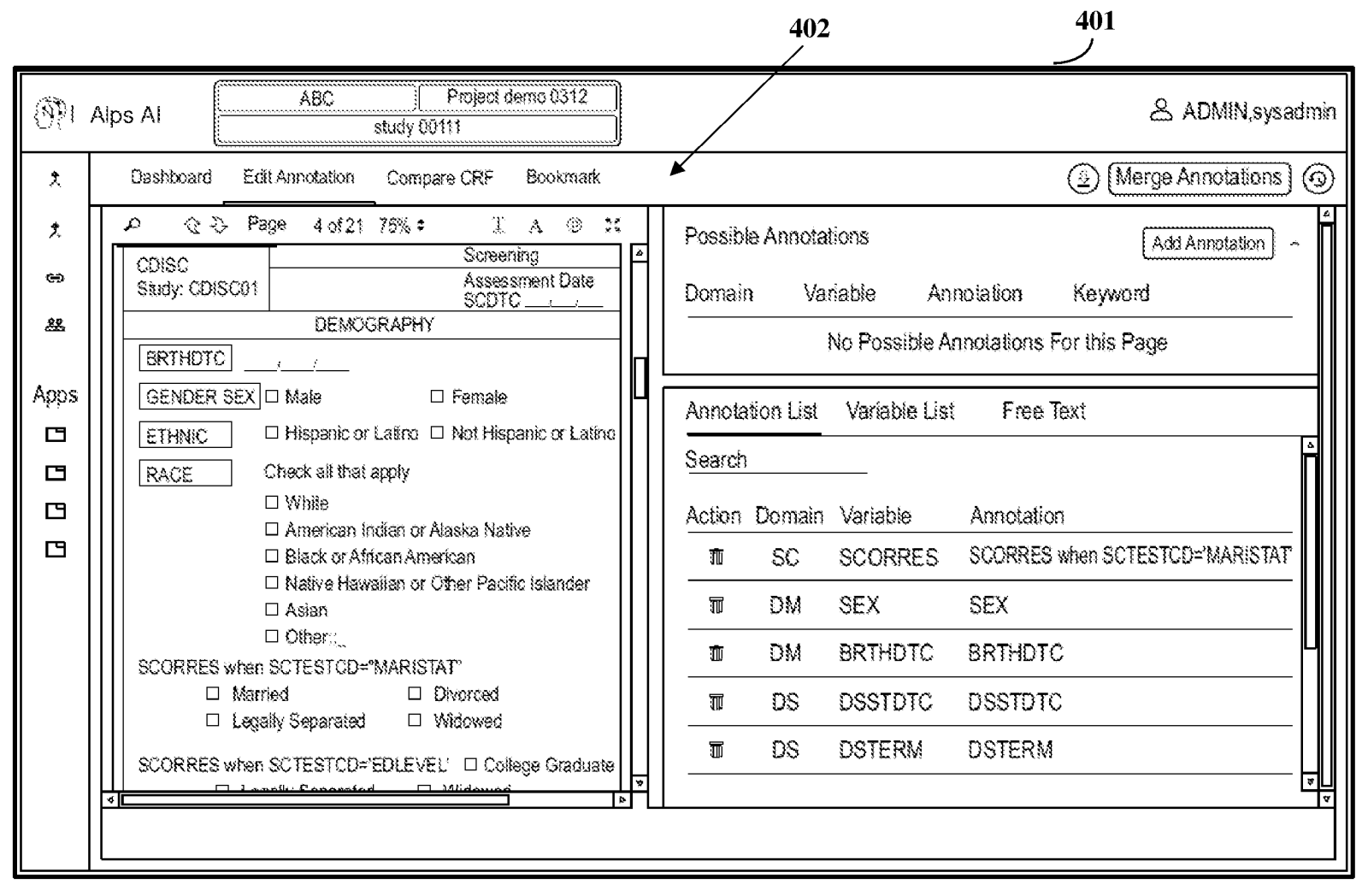

FIG. 4 exemplarily illustrates a screenshot of a graphical user interface 401 provided by the clinical data standards (CDS) automated system, displaying an electronic case report form (eCRF) 402 with possible annotations. The eCRF 402 comprises an "edit annotation screen". The CDS automated system automatically annotates the CRF based on natural language processing capabilities of the CDS automated system. The CDS automated system also allows a user to manually annotate the CRF, review the annotated CRF, and confirm to proceed to a subsequent screen. The eCRF 402 provides options to view a dashboard, edit annotation, compare the CRF, create and view bookmarks, merge annotations, and add annotations. The eCRF 402 comprises user information, for example, assessment date, date of birth, gender, ethnicity, race, scores etc., of the user. The eCRF 402 in the CDS automated system also displays possible annotations. The items listed under the possible annotations comprise, for example, domain, variable, annotation, and keyword. The eCRF 402 also displays an annotation list, a variable list, and free text. The options for a particular annotation search comprise, for example, action, domain, variable, and annotation.

Figure 5:
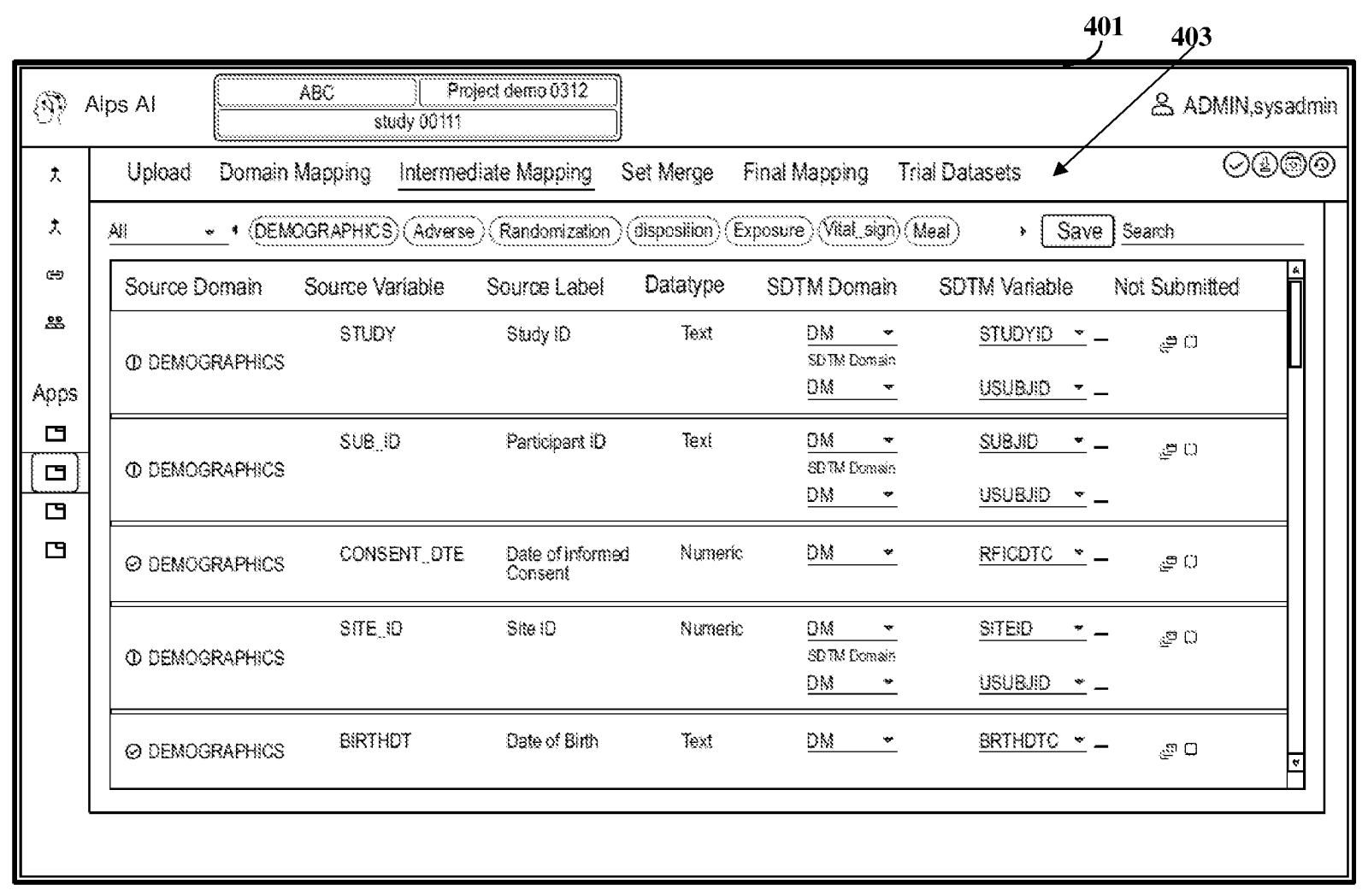

FIG. 5 exemplarily illustrates a screenshot of a graphical user interface 401 provided by the clinical data standards (CDS) automated system, displaying a smart mapper 403 that maps one or more raw datasets against a target study data tabulation model (SDTM) variable. The smart mapper 403 comprises an intermediate mapping screen as exemplarily illustrated in FIG. 5. The CDS automated system performs an automatic raw variable to SDTM variable mapping based on historical data. The clinical data standards automated system also allows a user to further edit the screen, review the screen, and confirm to proceed to a subsequent screen. The smart mapper 403 provides options to upload, perform domain mapping, perform an intermediate mapping, set merge, perform a final mapping, and view trial datasets. The smart mapper 403 also displays demographics of a particular user.

Figure 6:
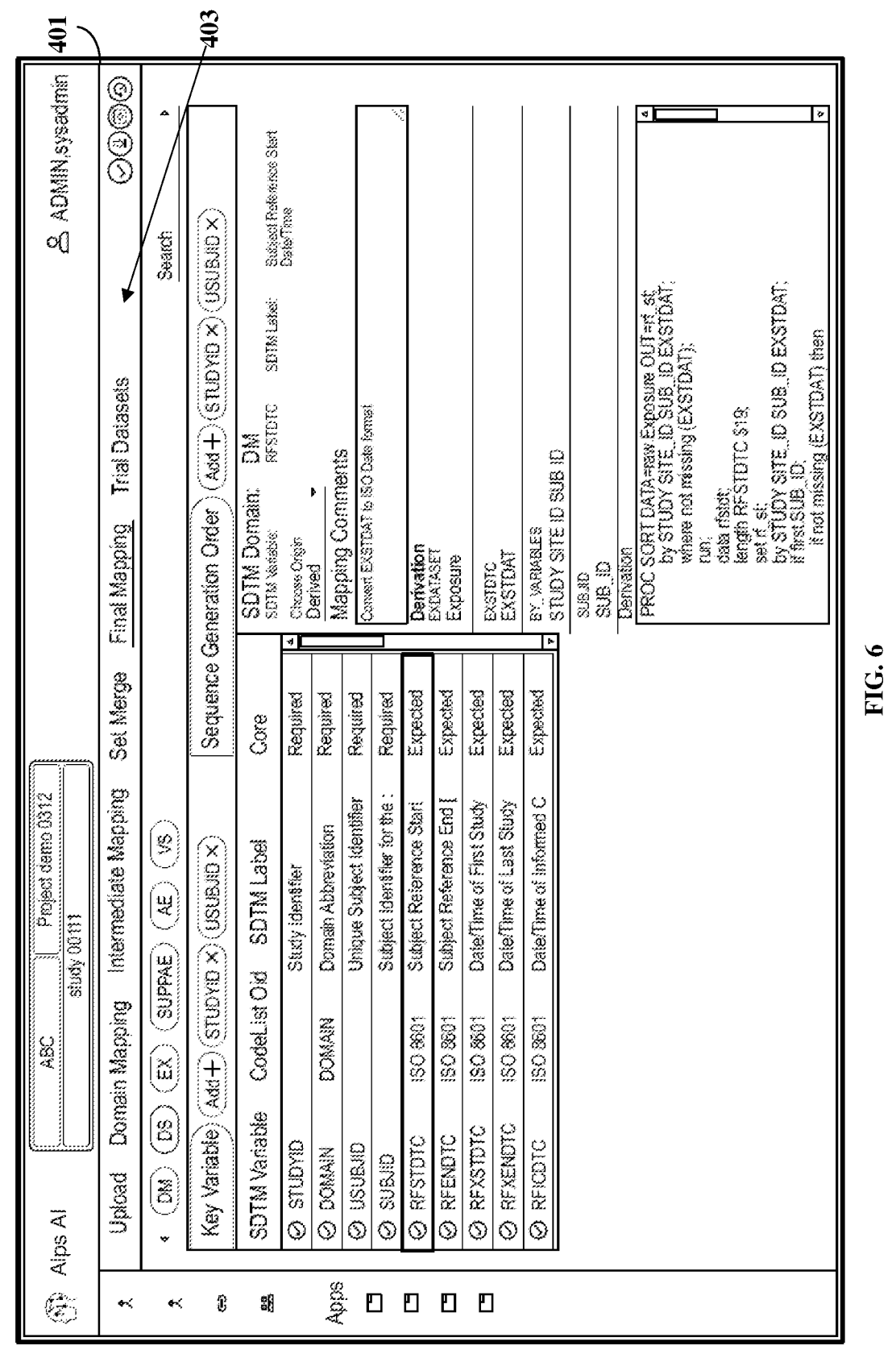

FIG. 6 exemplarily illustrates a screenshot of the smart mapper 403 displaying a mapping of one or more raw datasets against the target study data tabulation model (SDTM) variable with mapping comments. The smart mapper 403 comprises a final mapping screen as exemplarily illustrated in FIG. 6. The clinical data standards (CDS) automated system displays the standardized SDTM variable and its corresponding details with the derivation. The CDS automated system allows a user to modify the details as an option. The smart mapper 403 displays the final mapping along with the SDTM variables, mapping comments, and derivation variables.

Figure 7:
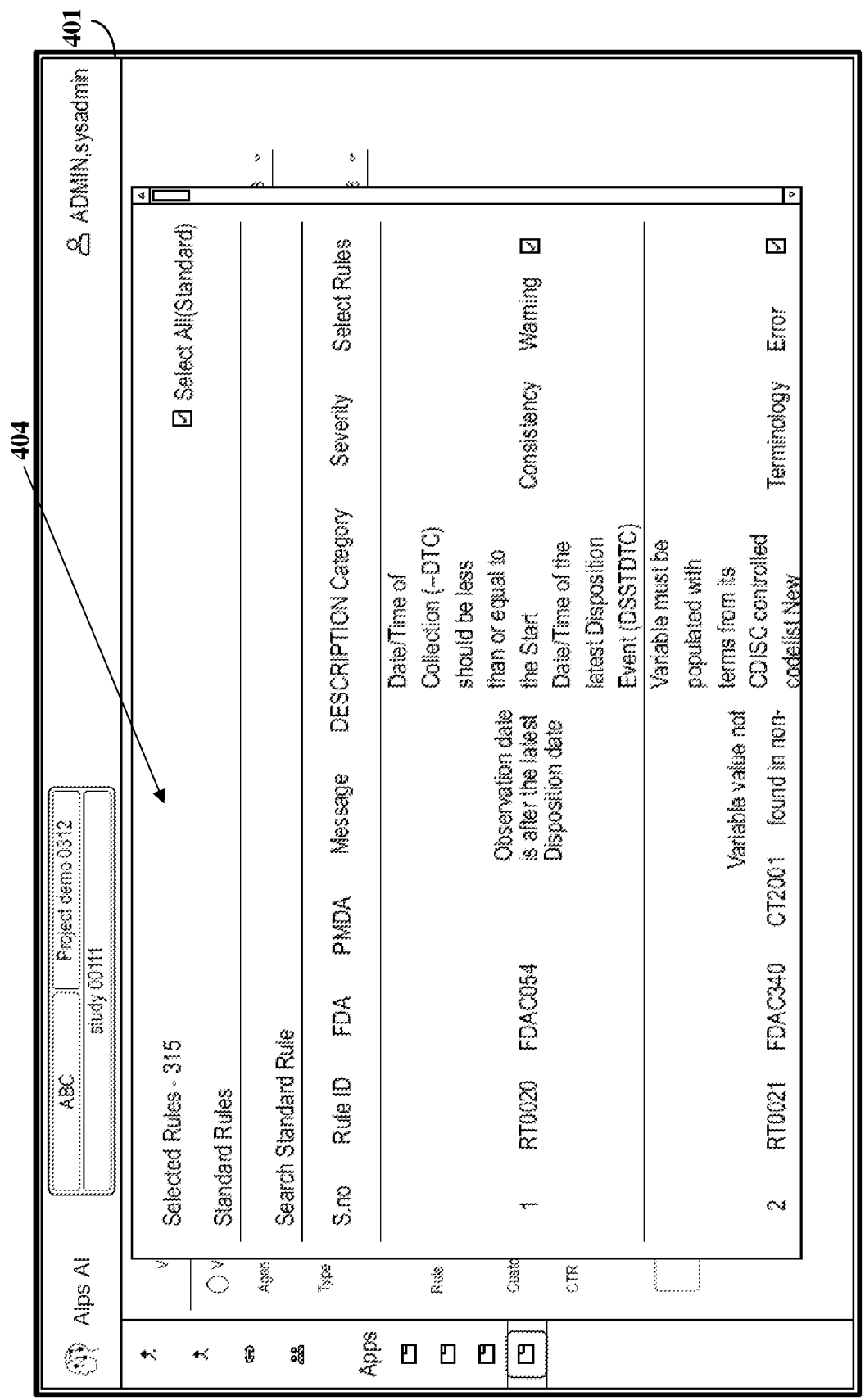
FIG. 7 exemplarily illustrates a screenshot of a graphical user interface provided by the clinical data standards automated system, displaying standard SDTM conformance rules listed for a particular study validation.

FIG. 7 exemplarily illustrates a screenshot of a graphical user interface provided by the clinical data standards automated system, displaying standard SDTM conformance rules listed for a particular study validation. In an embodiment, the validator of the CDS automated system renders a rule selection screen 404 to allow a user to select the SDTM conformance rules. The validator validates the selected SDTM conformance rules via the rule selection screen 404.

Figure 8:
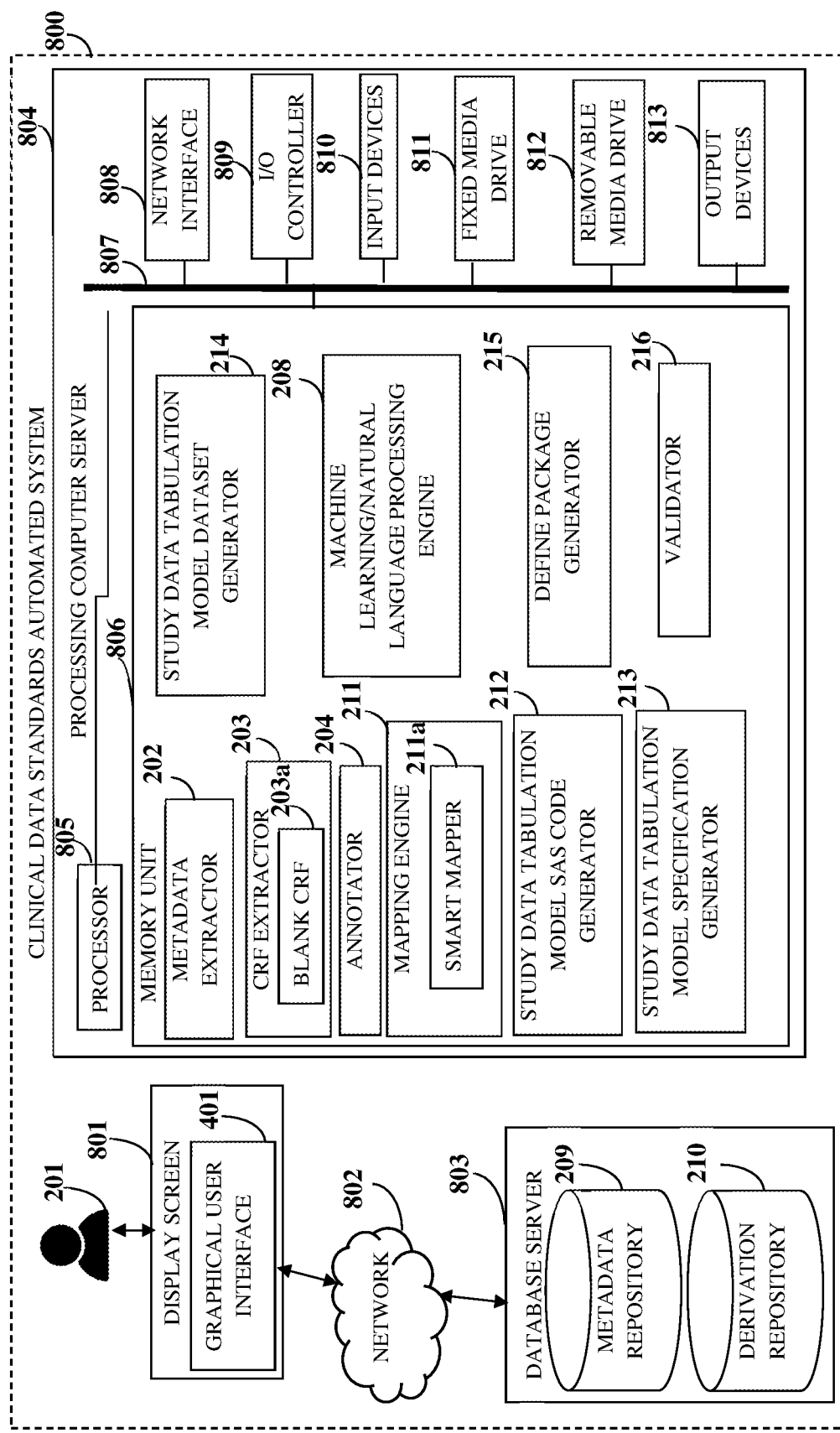
FIG. 8 illustrates an architectural block diagram of an exemplary implementation of the CDS automated system for automating clinical data standards and generating SDTM artifacts required for a regulatory submission process using a machine learning model and a natural language processing engine with minimal user intervention.

FIG. 8 illustrates an architectural block diagram of an exemplary implementation of the clinical data standards (CDS) automated system 800 for automating clinical data standards and generating study data tabulation model (SDTM) artifacts required for a regulatory submission process using a machine learning model and a natural language processing engine with minimal user intervention. As exemplarily illustrated in FIG. 8, the CDS automated system 800 is a computer implemented system comprising a processing computer server 804 and a database server 803 accessible via a network 802. The processing computer server 804 is a computer system that is programmable using high-level computer programming languages. In an embodiment, the processing computer server 804 uses programmed and purposeful hardware. The CDS automated system 800 allows a user to the access results generated by the processing computer server 804 via a display screen 801 implemented on a user device, for example, a personal computer, a tablet computing device, a mobile computer, a portable computing device, a laptop, a touch device, a workstation, a portable electronic device, a network enabled computing device, an interactive network enabled communication device, any other suitable computing equipment, combinations of multiple pieces of computing equipment, etc. In an embodiment, the CDS automated system 800 is configured as a web-based platform, for example, a website hosted on a server or a network of servers.

The clinical data standards (CDS) automated system 800 communicates with the processing computer server 804, the database server 803, and the user device via the network 802. The network 802 is, for example, the internet, an intranet, a wireless network, a communication network that implements Bluetooth® of Bluetooth Sig, Inc., a network that implements Wi-Fi® of Wi-Fi Alliance Corporation, an ultra-wideband communication network (UWB), a wireless universal serial bus (USB) communication network, a communication network that implements ZigBee® of ZigBee Alliance Corporation, a general packet radio service (GPRS) network, a mobile telecommunication network such as a global system for mobile (GSM) communications network, a code division multiple access (CDMA) network, a third generation (3G) mobile communication network, a fourth generation (4G) mobile communication network, a fifth generation (5G) mobile communication network, a long-term evolution (LTE) mobile communication network, a public telephone network, etc., a local area network, a wide area network, an internet connection network, an infrared communication network, etc., or a network formed from any combination of these networks.

In an embodiment, the clinical data standards (CDS) automated system 800 is accessible to a satellite internet of users, for example, through a broad spectrum of technologies and devices such as cellular phones, tablet computing devices, etc., with access to the internet. The CDS automated system 800 receives raw metadata from the users using user devices. The user devices are electronic devices, for example, personal computers, tablet computing devices, mobile computers, mobile phones, smartphones, portable computing devices, personal digital assistants, laptops, wearable computing devices such as the Google Glass® of Google Inc., the Apple Watch® of Apple Inc., etc., touch centric devices, client devices, portable electronic devices, network enabled computing devices, interactive network enabled communication devices, any other suitable computing equipment, combinations of multiple pieces of computing equipment, etc. In an embodiment, the user devices are hybrid computing devices that combine the functionality of multiple devices. Examples of a hybrid computing device comprise a cellular telephone that includes a media player functionality, a gaming device that includes a wireless communications capability, a cellular telephone that includes a document reader and multimedia functions, and a portable device that has network browsing, document rendering, and network communication capabilities.

As exemplarily illustrated in FIG. 8, the processing computer server 804 of the clinical data standards (CDS) automated system 800 comprises a non-transitory, computer readable storage medium, for example, a memory unit 806 for storing programs and data, and at least one processor 805 communicatively coupled to the non-transitory, computer readable storage medium. As used herein, "non-transitory computer readable storage medium" refers to all computer readable media that contain and store computer programs and data, except for a transitory, propagating signal. Examples of the computer-readable media comprise hard drives, solid state drives, optical discs or magnetic disks, memory chips, a read-only memory (ROM), a register memory, a processor cache, a random-access memory (RAM), etc. The non-transitory computer readable storage medium is configured to store computer program instructions defined by modules, for example, 202, 203, 204, 208, 211, 212, 213, 214, 215, 216, etc., of the CDS automated system 800. The modules 202, 203, 204, 208, 211, 212, 213, 214, 215, and 216 are installed and stored in the memory unit 806. The memory unit 806 is used for storing program instructions, applications, and data. The memory unit 806 is, for example, a random access memory (RAM) or another type of dynamic storage device that stores information and instructions for execution by the processor 805. The memory unit 806 also stores temporary variables and other intermediate information used during execution of the instructions by the processor 805. The processing computer server 804 further comprises a read only memory (ROM) or another type of static storage device that stores static information and instructions for the processor 805.

The processor 805 is configured to execute the computer program instructions defined by the modules, for example, 202, 203, 204, 208, 211, 212, 213, 214, 215, 216 etc., of the clinical data standards (CDS) automated system 800. The processor 805 refers to any of one or more microprocessors, central processing unit (CPU) devices, finite state machines, computers, microcontrollers, digital signal processors, logic, a logic device, a user circuit, an application specific integrated circuit (ASIC), a field-programmable gate array (FPGA), a chip, etc., or any combination thereof, capable of executing computer programs or a series of commands, instructions, or state transitions. In an embodiment, the processor 805 is implemented as a processor set comprising, for example, a programmed microprocessor and a math or graphics co-processor. The processor 805 is selected, for example, from the Intel® processors such as the Itanium® microprocessor or the Pentium® processors, Advanced Micro Devices (AMD®) processors such as the Athlon® processor, UltraSPARC® processors, microSPARC® processors, Hp® processors, International Business Machines (IBM®) processors such as the PowerPC® microprocessor, the MIPS® reduced instruction set computer (RISC) processor of MIPS Technologies, Inc., RISC based computer processors of ARM Holdings, Motorola® processors, Qualcomm® processors, etc. The CDS automated system 800 is not limited to employing a processor 805. In an embodiment, the CDS automated system 800 employs a controller or a microcontroller.

As exemplarily illustrated in FIG. 8, the clinical data standards (CDS) automated system 800 further comprises a data bus 807, a network interface 808, an input/output (I/O) controller 809, input devices 810, a fixed media drive 811 such as a hard drive, a removable media drive 812 for receiving removable media, output devices 813, etc. The data bus 807 permits communications between the modules, for example, 202, 203, 204, 208, 211, 212, 213, 214, 215, 216, etc., of the CDS automated system 800. The network interface 808 enables connection of the CDS automated system 800 to the network 802. In an embodiment, the network interface 808 is provided as an interface card also referred to as a line card. The network interface 808 comprises, for example, one or more of an infrared (IR) interface, an interface implementing Wi-Fi® of Wi-Fi Alliance Corporation, a universal serial bus (USB) interface, a FireWire® interface of Apple Inc., an Ethernet interface, a frame relay interface, a cable interface, a digital subscriber line (DSL) interface, a token ring interface, a peripheral controller interconnect (PCI) interface, a local area network (LAN) interface, a wide area network (WAN) interface, interfaces using serial protocols, interfaces using parallel protocols, Ethernet communication interfaces, asynchronous transfer mode (ATM) interfaces, a high speed serial interface (HSSI), a fiber distributed data interface (FDDI), interfaces based on a transmission control protocol (TCP)/internet protocol (IP), interfaces based on wireless communications technology such as satellite technology, radio frequency (RF) technology, near field communication, etc. The I/O controller 809 controls input actions and output actions performed by the CDS automated system 800.

The display screen 801, via the graphical user interface (GUI) 401, displays raw metadata, a blank case report form (CRF) 203a, the electronic CRF (eCRF) with possible annotations, the smart mapper, the rule selection screen, etc. The display screen 801 is, for example, a video display, a liquid crystal display, a plasma display, an organic light emitting diode (OLED) based display, etc. The clinical data standards (CDS) automated system 800 provides the GUI 401 on the display screen 801. The GUI 401 is, for example, an online web interface, a web based downloadable application interface, a mobile based downloadable application interface, etc. The display screen 801 displays the GUI 401. The input devices 810 are used for inputting data into the CDS automated system 800. The input devices 810 are, for example, a keyboard such as an alphanumeric keyboard, a microphone, a joystick, a pointing device such as a computer mouse, a touch pad, a light pen, a physical button, a touch sensitive display device, a track ball, a pointing stick, any device capable of sensing a tactile input, etc. The output devices 813 output the results of operations performed by the CDS automated system 800.

The modules of the clinical data standards (CDS) automated system 800 comprise the metadata extractor 202, the case report form (CRF) extractor 203, the annotator 204, the mapping engine 211, multiple study data tabulation model (SDTM) generators, for example, 212, 213, and 214, the define package generator 215, the validator 216, and the machine learning (ML)/natural language processing (NLP) engine 208 constituted by the ML model 206 and the NLP engine 207 as exemplarily illustrated in FIG. 2. In an embodiment as exemplarily illustrated in FIG. 8, these modules are stored in the memory unit 806 of the processing computer server 804. The metadata extractor 202 extracts metadata from one or more raw datasets automatically using NLP and feeds the extracted metadata into the ML model 206. The NLP engine 207 in the ML/NLP engine 208 preprocesses text information before feeding the text information into the ML model 206. The CRF extractor 203 pre-fills the extracted metadata in a blank CRF 203a. The annotator 204 automatically predicts and annotates contents in the blank CRF 203a and the extracted metadata. The annotator 204 also records any unknown data from a user as new learnings for subsequent studies thereby reducing user intervention. The machine learning model 206 in the ML/NLP engine 208 predicts appropriate CRF annotations based on annotated metadata information available in the CDS automated system 800 and the information acquired from previous learnings.

The mapping engine 211 comprises the smart mapper 211a as disclosed in the detailed description of FIG. 2. The smart mapper 211a maps one or more raw datasets against a target study data tabulation model (SDTM) variable based on the extracted metadata, for example, an annotated case report form (CRF), available in the clinical data standards (CDS) automated system 800 and information acquired from previous learnings. In an embodiment, the SDTM generators comprise the study data tabulation model (SDTM) statistical analysis system (SAS) code generator 212, the SDTM specification generator 213, and the SDTM dataset generator 214 as disclosed in the detailed description of FIG. 2. The SDTM SAS code generator 212 generates an SDTM SAS code based on the mapping. The SDTM specification generator 213 and the SDTM dataset generator 214 generate an SDTM specification and SDTM datasets based on the mapping, that is, the mapped raw metadata, respectively. The machine learning model 206 identifies an appropriate derivation and generates the SAS code based on the derivation. In an embodiment, the derivation is obtained from the mapped metadata available in the CDS automated system 800. The define package generator 215 generates a define package based on the annotated metadata information and the mapping available in the CDS automated system 800. The define package comprises define.xml files. The validator 216 validates the generated define package and the SDTM artifacts generated throughout the entire cycle and generates validation reports in real time. The define package further comprises a mapping specification, the SDTM datasets, the annotated CRF, etc., for a submission purpose. The SDTM artifacts comprises, for example, a define.xml file, stylesheets, SDTM datasets, an annotated CRF, a reviewers guide, and other supporting documents. In an embodiment, the SDTM artifacts comprise the SDTM statistical analysis system (SAS) code, the SDTM specification, and one or more SDTM datasets.

The clinical data standards (CDS) automated system 800 stores the metadata and the identified derivations from the machine learning model 206 in a metadata repository 209 and a derivation repository 210 of the database server 803 respectively. The metadata repository 209 and the derivation repository 210 of the CDS automated system 800 can be any storage area or medium that can be used for storing data and files. In an embodiment, the CDS automated system 800 stores the received information in external databases, for example, a structured query language (SQL) data store or a not only SQL (NoSQL) data store such as the Microsoft® SQL Server®, the Oracle® servers, the MySQL® database of MySQL AB Company, the mongoDB® of MongoDB, Inc., the Neo4j graph database of Neo Technology Corporation, the Cassandra database of the Apache Software Foundation, the HBase™ database of the Apache Software Foundation, etc. In another embodiment, the metadata repository 209 and the derivation repository 210 can be a location on a file system. In another embodiment, the metadata repository 209 and the derivation repository 210 are remotely accessible by the CDS automated system 800 via the network 802. In another embodiment, the metadata repository 209 and the derivation repository 210 are configured as cloud-based databases implemented in a cloud computing environment, where computing resources are delivered as a service over the network 802.

Computer applications and programs are used for operating the modules of the clinical data standards (CDS) automated system 800. The programs are loaded onto the fixed media drive 811 and into the memory unit 806 of the processing computer server 804 via the removable media drive 812. In an embodiment, the computer applications and programs are loaded directly onto the processing computer server 804 via the network 802. The processor 805 executes an operating system, for example, the Linux® operating system, the Unix® operating system, any version of the Microsoft® Windows® operating system, the Mac OS of Apple Inc., the IBM® OS/2, VxWorks® of Wind River Systems, Inc., QNX Neutrino® developed by QNX Software Systems Ltd., the Palm OS®, the Solaris operating system developed by Sun Microsystems, Inc., etc. The processing computer server 804 employs the operating system for performing multiple tasks. The operating system is responsible for management and coordination of activities and sharing of resources of the processing computer server 804. The operating system further manages security of the processing computer server 804, peripheral devices connected to the processing computer server 804, and network connections. The operating system employed on the processing computer server 804 recognizes, for example, inputs provided by a user of the CDS automated system 800 using one of the input devices 810, the output devices 813, files, and directories stored locally on the fixed media drive 811. The operating system on the processing computer server 804 executes different programs using the processor 805. The processor 805 and the operating system together define a computer platform for which application programs in high level programming languages are written.

The processor 805 of the processing computer server 804 retrieves instructions defined by the metadata extractor 202, the case report form (CRF) extractor 203, the annotator 204, the mapping engine 211, the study data tabulation model (SDTM) statistical analysis system (SAS) code generator 212, the SDTM specification generator 213, the SDTM dataset generator 214, the machine learning/natural language processing engine 208, the define package generator 215, and the validator 216 for performing respective functions disclosed above. The processor 805 retrieves instructions for executing the modules, for example, 202, 203, 204, 208, 211, 212, 213, 214, 215, 216, etc., of the clinical data standards (CDS) automated system 800 from the memory unit 806. A program counter determines the location of the instructions in the memory unit 806. The program counter stores a number that identifies the current position in the program of each of the modules, for example, 202, 203, 204, 208, 211, 212, 213, 214, 215, 216, etc., of the CDS automated system 800. The instructions fetched by the processor 805 from the memory unit 806 after being processed are decoded. The instructions are stored in an instruction register in the processor 805. After processing and decoding, the processor 805 executes the instructions, thereby performing one or more processes defined by those instructions.

At the time of execution, the instructions stored in the instruction register are examined to determine the operations to be performed. The processor 805 then performs the specified operations. The operations comprise arithmetic operations and logic operations. The operating system performs multiple routines for performing a number of tasks required to assign the input devices 810, the output devices 813, and the memory unit 806 for execution of the modules, for example, 202, 203, 204, 208, 211, 212, 213, 214, 215, 216, etc., of the clinical data standards (CDS) automated system 800. The tasks performed by the operating system comprise, for example, assigning memory to the modules, for example, 202, 203, 204, 208, 211, 212, 213, 214, 215, 216, etc., of the CDS automated system 800 and to data used by the CDS automated system 800, moving data between the memory unit 806 and disk units, and handling input/output operations. The operating system performs the tasks on request by the operations and after performing the tasks, the operating system transfers the execution control back to the processor 805. The processor 805 continues the execution to obtain one or more outputs. The outputs of the execution of the modules, for example, 202, 203, 204, 208, 211, 212, 213, 214, 215, 216, etc., of the CDS automated system 800 are displayed to a user of the CDS automated system 800 on the output devices 813. In an embodiment, one or more portions of the CDS automated system 800 are distributed across one or more computer systems (not shown) coupled to the network 802.

The non-transitory, computer readable storage medium disclosed herein stores computer program codes comprising instructions executable by at least one processor 805 for automating clinical data standards and generating study data tabulation model (SDTM) artifacts required for a regulatory submission process using a machine learning (ML) model 206 and a natural language processing engine 207 with minimal user intervention. The computer program codes comprise a first computer program code for extracting metadata from multiple raw datasets automatically using natural language processing and feeding the extracted metadata into the ML model 206; a second computer program code for predicting one or more automatic case report form (CRF) annotations on the extracted metadata using the ML model 206 and recording new learnings in the clinical data standards (CDS) automated system with minimal user intervention; a third computer program code for mapping one or more raw datasets against a target SDTM variable based on the extracted metadata available in the CDS automated system and information acquired from previous learnings; a fourth computer program code for generating an SDTM statistical analysis system (SAS) code, an SDTM specification, and one or more SDTM datasets based on the mapping or the mapped metadata; a fifth computer program code for generating a define package based on annotated metadata information available in the CDS automated system; and a sixth computer program code for validating the generated define package and one or more SDTM artifacts generated throughout the entire cycle and for generating validation reports in real time.

The computer program instructions implement the processes of various embodiments disclosed above and perform additional steps that may be required and contemplated for automating clinical data standards and generating study data tabulation model (SDTM) artifacts required for a regulatory submission process using a machine learning (ML) model 206 and a natural language processing (NLP) engine 207 with minimal user intervention. When the computer program instructions are executed by the processor 805, the computer program instructions cause the processor 805 to perform the steps of the method for automating clinical data standards and generating SDTM artifacts required for the regulatory submission process using the ML model 206 and the NLP engine 207 with minimal user intervention as disclosed in the detailed descriptions of FIGS. 1-2. In an embodiment, a single piece of computer program code comprising computer program instructions performs one or more steps of the method disclosed in the detailed descriptions of FIGS. 1-2. The processor 805 retrieves these computer program instructions and executes them.

It is apparent in different embodiments that the various methods, algorithms, and computer readable programs disclosed herein are implemented on non-transitory, computer readable storage media appropriately programmed for computing devices. The non-transitory, computer readable storage media participate in providing data, for example, instructions that are read by a computer, a processor, or a similar device. In different embodiments, the "non-transitory, computer readable storage media" also refers to a single medium or multiple media, for example, a centralized database, a distributed database, and/or associated caches and servers that store one or more sets of instructions that are read by a computer, a processor, or a similar device. The "non-transitory, computer readable storage media" also refer to any medium capable of storing or encoding a set of instructions for execution by a computer, a processor, or a similar device and that causes a computer, a processor, or a similar device to perform any one or more of the steps of the methods disclosed herein.

In an embodiment, the computer programs that implement the methods and algorithms disclosed herein are stored and transmitted using a variety of media, for example, the computer readable media in various manners. In an embodiment, hard-wired circuitry or custom hardware is used in place of, or in combination with, software instructions for implementing the processes of various embodiments. Therefore, the embodiments are not limited to any specific combination of hardware and software. The computer program codes comprising computer executable instructions can be implemented in any programming language. Examples of programming languages that can be used comprise C, C++, C#, Java®, JavaScript®, Fortran, Ruby, Perl®, Python®, Visual Basic®, hypertext preprocessor (PHP), Microsoft® .NET, Objective-C®, etc. Other object-oriented, functional, scripting, and/or logical programming languages can also be used. In an embodiment, the computer program codes or software programs are stored on or in one or more mediums as object code. In another embodiment, various aspects of the method and the system disclosed herein are implemented in a non-programmed environment comprising documents created, for example, in a hypertext markup language (HTML), an extensible markup language (XML), or other format that render aspects of a graphical user interface (GUI) or perform other functions, when viewed in a visual area or a window of a browser program. In another embodiment, various aspects of the method and the system disclosed herein are implemented as programmed elements, or non-programmed elements, or any suitable combination thereof.

Where databases are described such as the metadata repository 209 and the derivation repository 210 of the database server 803, it will be understood by one of ordinary skill in the art that (i) alternative database structures to those described may be employed, and (ii) other memory structures besides databases may be employed. Any illustrations or descriptions of any sample databases disclosed herein are illustrative arrangements for stored representations of information. In an embodiment, any number of other arrangements are employed besides those suggested by tables illustrated in the drawings or elsewhere. Similarly, any illustrated entries of the databases represent exemplary information only; one of ordinary skill in the art will understand that the number and content of the entries can be different from those disclosed herein. In another embodiment, despite any depiction of the databases as tables, other formats including relational databases, object-based models, and/or distributed databases are used to store and manipulate the data types disclosed herein. Object methods or behaviors of a database can be used to implement various processes such as those disclosed herein. In another embodiment, the databases are, in a known manner, stored locally or remotely from a device that accesses data in such a database. In embodiments where there are multiple databases in the system, the databases are integrated to communicate with each other for enabling simultaneous updates of data linked across the databases, when there are any updates to the data in one of the databases.

The method and the system disclosed herein can be configured to work in a network environment comprising one or more computers that are in communication with one or more devices via a network. In an embodiment, the computers communicate with the devices directly or indirectly, via a wired medium or a wireless medium such as the Internet, a local area network (LAN), a wide area network (WAN) or the Ethernet, a token ring, or via any appropriate communications mediums or combination of communications mediums. Each of the devices comprises processors, examples of which are disclosed above, that are adapted to communicate with the computers. In an embodiment, each of the computers is equipped with a network communication device, for example, a network interface card, a modem, or other network connection device suitable for connecting to a network. Each of the computers and the devices executes an operating system, examples of which are disclosed above. While the operating system may differ depending on the type of computer, the operating system provides the appropriate communications protocols to establish communication links with the network. Any number and type of machines may be in communication with the computers.

The method and the system disclosed herein are not limited to a particular computer system platform, processor, operating system, or network. In an embodiment, one or more aspects of the method and the system disclosed herein are distributed among one or more computer systems, for example, servers configured to provide one or more services to one or more client computers, or to perform a complete task in a distributed system. For example, one or more aspects of the method and the system disclosed herein are performed on a client-server system that comprises components distributed among one or more server systems that perform multiple functions according to various embodiments. These components comprise, for example, executable, intermediate, or interpreted code, which communicate over a network using a communication protocol. The method and the system disclosed herein are not limited to be executable on any particular system or group of systems, and are not limited to any particular distributed architecture, network, or communication protocol.

The foregoing examples and illustrative implementations of various embodiments have been provided merely for explanation and are in no way to be construed as limiting of the method and the system disclosed herein. While method and the system have been described with reference to various embodiments, it is understood that the words, which have been used herein, are words of description and illustration, rather than words of limitation. Furthermore, although the method and the system have been described herein with reference to particular means, materials, techniques, and embodiments, the method and the system are not intended to be limited to the particulars disclosed herein; rather, the method and the system extend to all functionally equivalent structures, methods and uses, such as are within the scope of the appended claims. While multiple embodiments are disclosed, it will be understood by those skilled in the art, having the benefit of the teachings of this specification, that method and the system disclosed herein are capable of modifications and other embodiments may be effected and changes may be made thereto, without departing from the scope and spirit of the method and the system disclosed herein.

I claim:

1. A method for automating clinical data standards and generating study data tabulation model (SDTM) artifacts required for a regulatory submission process using a machine learning model and a natural language processing engine, the method employing a clinical data standards automated system comprising at least one processor configured to execute computer program instructions for performing the method comprising:
   extracting metadata from raw datasets automatically using natural language processing and feeding the extracted metadata into the machine learning model, by the clinical data standards automated system;
   pre-filling the extracted metadata into a blank case report form (CRF), by the clinical data standards automated system;
   predicting automatic case report form (CRF) annotations on the extracted metadata using the machine learning model, based on annotated metadata information available in the clinical data standards automated system and information acquired from previous learnings, and recording new learnings into the clinical data standards automated system with the minimal user intervention, by the clinical data standards automated system, wherein the previous learnings are learnings recorded by the clinical data standards automated system based on the annotated metadata information manually acquired from a user into the blank case report form (CRF) at beginning of a clinical trial process, wherein the predicted CRF annotations and corresponding text and attributes are sent to an application in the clinical data standards automated system, and wherein the application inserts CRF annotations into the blank CRF pre-filled with the extracted metadata, based on prediction from the machine learning model;
   mapping the raw datasets against a target SDTM variable based on the extracted metadata available in the clinical data standards automated system and information acquired from the previous learnings, by the clinical data standards automated system;
   generating an SDTM statistical analysis system (SAS) code based on the mapping, the prediction, and derivations, an SDTM specification, and SDTM datasets based on the mapping, by the clinical data standards automated system, wherein the clinical data standards automated system predicts derivation logic from a derivation repository based on mapping combinations, study design, and the extracted metadata, and wherein the generated SDTM SAS code is executable outside the clinical data standards automated system in a SAS application;
   generating a define package based on annotated metadata information and the mapping available in the clinical data standards automated system, by the clinical data standards automated system, wherein the define package is a Clinical Data Interchange Standards Consortium (CDISC) standard "define.xml" file and a reviewer's guide, and wherein the "define.xml" file is an extensible markup language (XML) document that describes structure and content of data collected during the clinical trial process; and
   validating the generated define package and SDTM artifacts generated during a development and review cycle, and generating validation reports in real time, by the clinical data standards automated system, wherein the SDTM artifacts comprise the generated define.xml files, stylesheets, the SDTM datasets, an annotated case report form (CRF), the reviewers guide, and supporting documents, and wherein the validations are based on the Clinical Data Interchange Standards Consortium (CDISC) or United States Food and Drug Administration (FDA)-published validation rules.

2. The method of claim 1, wherein the natural language processing engine preprocesses text information before feeding the text information into the machine learning model.

3. The method of claim 1, wherein the machine learning model is used to identify the derivations and generate the study data tabulation model (SDTM) statistical analysis system (SAS) code based on the derivations.

4. A clinical data standards automated system for automating clinical data standards and generating study data tabulation model (SDTM) artifacts required for a regulatory submission process using a machine learning model and a natural language processing engine, the system comprising
   a non-transitory, computer readable storage medium configured to store computer program instructions defined by modules of the clinical data standards automated system; and
   at least one processor communicatively coupled to the non-transitory computer readable storage media, the at least one processor configured to execute the computer program instructions defined by the modules of the clinical data standards automated system, the modules comprising:
      a metadata extractor for extracting metadata from raw datasets automatically using natural language processing and feeding the extracted metadata into the machine learning model;
      a case report form extractor for pre-filling the extracted metadata into a blank case report form (CRF);
      an annotator for automatically predicting and annotating contents in the blank CRF and the extracted metadata, using the machine learning model, based on annotated metadata information available in the clinical data standards automated system and information acquired from previous learnings, and recording new learnings into the clinical data standards automated system with the minimal user intervention, wherein the previous learnings are learnings recorded by the clinical data standards automated system based on the annotated metadata information manually acquired from a user into the blank case report form (CRF) at beginning of a clinical trial process, wherein the predicted CRF annotations and corresponding text and attributes are sent to an application in the clinical data standards automated system, and wherein the application inserts CRF annotations into the blank CRF pre-filled with the extracted metadata, based on prediction from the machine learning model;
      a smart mapper for mapping the raw datasets against a target SDTM variable based on the extracted metadata available in the clinical data standards automated system and information acquired from the previous learnings;

a plurality of SDTM generators for generating an SDTM SAS code based on the mapping, the prediction, and derivations, an SDTM specification, and SDTM datasets based on the mapping, wherein the clinical data standards automated system predicts derivation logic from a derivation repository based on mapping combinations, study design, and the extracted metadata, and wherein the generated SDTM SAS code is executable outside the clinical data standards automated system in a SAS application;

a define package generator for generating a define package based on annotated metadata information and the mapping available in the clinical data standards automated system, wherein the define package is a Clinical Data Interchange Standards Consortium (CDISC) standard "define.xml" file and a reviewer's guide, and wherein the "define.xml" file is an extensible markup language (XML) document that describes structure and content of data collected during the clinical trial process; and a validator for validating the generated define package and the SDTM artifacts generated during a development and review cycle, and generating validation reports in real time, wherein the SDTM artifacts comprise the generated define.xml files, stylesheets, the SDTM datasets, an annotated case report form (CRF), the reviewers guide, and supporting documents, and wherein the validations are based on the Clinical Data Interchange Standards Consortium (CDISC) or United States Food and Drug Administration (FDA)-published validation rules.

5. The system of claim 4, wherein the natural language processing engine preprocesses text information before feeding the text information into the machine learning model.

6. The system of claim 4, wherein the machine learning model is used to identify the derivations and generate the study data tabulation model (SDTM) statistical analysis system (SAS) code based on the derivations.

7. A non-transitory, computer readable storage medium having embodied thereon, computer program codes comprising instructions executable by at least one processor for automating clinical data standards and generating study data tabulation model (SDTM) artifacts required for a regulatory submission process using a machine learning model and a natural language processing engine, the computer program codes comprising:

a first computer program code for extracting metadata from raw datasets automatically using natural language processing and feeding the extracted metadata into the machine learning model;

a second computer program code for pre-filling the extracted metadata into a blank case report form (CRF);

a third computer program code for predicting automatic case report form (CRF) annotations on the extracted metadata using the machine learning model, based on annotated metadata information available in the clinical data standards automated system and information acquired from previous learnings, and for recording new learnings into the clinical data standards automated system with the minimal user intervention, wherein the previous learnings are learnings recorded by the clinical data standards automated system based on the annotated metadata information manually acquired from a user into the blank case report form (CRF) at beginning of a clinical trial process, wherein the predicted CRF annotations and corresponding text and attributes are sent to an application in a clinical data standards automated system, and wherein the application inserts CRF annotations into the blank CRF pre-filled with the extracted metadata, based on prediction from the machine learning model;

a fourth computer program code for mapping the raw datasets against a target SDTM variable based on the extracted metadata available in the clinical data standards automated system and information acquired from the previous learnings;

a fifth computer program code for generating an SDTM statistical analysis system (SAS) code based on the mapping, the prediction, and derivations, an SDTM specification, and SDTM datasets based on the mapping, wherein the clinical data standards automated system predicts derivation logic from a derivation repository based on mapping combinations, study design, and the extracted metadata, and wherein the generated SDTM SAS code is executable outside the clinical data standards automated system in a SAS application;

a sixth computer program code for generating a define package based on annotated metadata information and the mapping available in the clinical data standards automated system, wherein the define package is a Clinical Data Interchange Standards Consortium (CDISC) standard "define.xml" file and a reviewer's guide, and wherein the "define.xml" file is an extensible markup language (XML) document that describes structure and content of data collected during the clinical trial process; and a seventh computer program code for validating the generated define package and the SDTM artifacts generated during a development and review cycle, and for generating validation reports in real time, wherein the SDTM artifacts comprise the generated define.xml files, stylesheets, the SDTM datasets, an annotated case report form (CRF), the reviewers guide, and supporting documents, and wherein the validations are based on the Clinical Data Interchange Standards Consortium (CDISC) or United States Food and Drug Administration (FDA)-published validation rules.

* * * * *